United States Patent [19]
Turner et al.

[11] Patent Number: 5,948,621
[45] Date of Patent: Sep. 7, 1999

[54] DIRECT MOLECULAR PATTERNING USING A MICRO-STAMP GEL

[75] Inventors: David C. Turner, Waldorf, Md.; Brett Martin, Alexandria, Va.; Bruce P. Gaber, Bethesda, Md.

[73] Assignee: The United States of America as represented by the Secretary of the Navy, Washington, D.C.

[21] Appl. No.: 08/940,178

[22] Filed: Sep. 30, 1997

[51] Int. Cl.⁶ .............................. C12Q 1/68; C12Q 1/00; C12Q 1/70; B41M 3/12
[52] U.S. Cl. .................................. 435/6; 427/150; 435/4; 435/5; 435/7.1
[58] Field of Search .................................. 427/150; 435/4, 435/5, 6, 7.1

[56] References Cited

U.S. PATENT DOCUMENTS

| | | | |
|---|---|---|---|
| 4,970,145 | 11/1990 | Bennetto et al. | 435/14 |
| 5,192,507 | 3/1993 | Taylor et al. | 422/68.1 |
| 5,468,620 | 11/1995 | Molloy et al. | 435/7.1 |
| 5,474,915 | 12/1995 | Dordick et al. | 435/72 |
| 5,512,131 | 4/1996 | Kumar et al. | 156/655.1 |
| 5,554,339 | 9/1996 | Cozzette et al. | 422/50 |
| 5,567,301 | 10/1996 | Stetter et al. | 205/777.5 |
| 5,776,748 | 7/1998 | Singhvi et al. | 435/180 |

FOREIGN PATENT DOCUMENTS

| | | |
|---|---|---|
| 361090050 | 5/1986 | Japan . |
| 405133928 | 5/1993 | Japan . |

*Primary Examiner*—Robert A. Wax
*Assistant Examiner*—Einar Stole
*Attorney, Agent, or Firm*—Thomas E. McDonnell; Barry A. Edelberg

[57] ABSTRACT

A stamp for transferring molecules and molecular patterns to a substrate surface includes a backing and a polymeric gel bound to the backing and loaded with the a molecular species. Where the molecule to be patterned is a biomolecule, such as a protein or nucleic acid, the polymeric gel is typically a hydrogel. Exemplary hydrogels include sugar-based polyacrylates and polyacrylamides.

21 Claims, 5 Drawing Sheets

DIRECT MOLECULAR PATTERNING USING A MICRO-STAMP GEL

BACKGROUND OF THE INVENTION

1. Field of the Invention

The present invention relates generally to the selective attachment of molecules to surfaces and more specifically to the selective patterning of molecules upon surfaces.

2. Description of the Background Art

There is considerable interest in the biosensor and medical diagnostic communities in developing multiplexed immunosensors for the simultaneous detection of multiple antigens. The key feature of immunosensors is the coupling of an antibody or antigen to a solid support which facilitates the binding and separation of antibodies or antigens from a sample for detection. Single analyte immunoassays and sensors have been successfully developed to detect and measure pharmaceuticals, biomolecules, explosives and environmental toxins. However, the widespread exploitation of this technology has been limited by a number of problems. Prime among these problems are the non-specific binding of biomolecules to the solid support, reproducible device fabrication, rapid, simultaneous detection of a number of analytes, and miniaturization of the immunosensor for field use. Strategies have been developed to deal with non-specific binding by blocking the surface regions which do not contain coupled antibody or antigen through coating of those surface areas with proteins such as BSA, streptavidin or deglycosylated forms of avidin or through novel encapsulation and antibody labeling strategies. The needs for miniaturization and multiple analyte detection are the driving forces behind efforts to develop array biosensors which have a number of different antibodies coupled to a solid support. Development of such a biosensor requires the immobilization of dense, well-resolved arrays of the antibodies to maximize antigen binding. Consequently, novel deposition and immobilization techniques which minimize non-specific binding will have to be employed. Current efforts to fabricate such a device involve the use of photolithographic techniques and jet printing to couple multiple proteins and other biomolecules, such as DNA, to solid supports in high resolution patterns.

SUMMARY OF THE INVENTION

Accordingly, it is an object of this invention to reproducibly form surfaces having a pattern of one or more molecular species bound thereto.

It is a another object of the present invention to immobilize a dense, well-resolved array of biomolecules on a surface.

It is a further object of the present invention to permit fabrication of compact biosensors able to simultaneously assay for a plurality of distinct biomolecular species.

These and additional objects of the invention are accomplished by a macromolecular stamp made using a polymeric gel. One surface of the polymeric gel is bound to a solid substrate. Another surface of the polymeric gel is exposed and is patterned to include raised regions and indented regions. The raised regions include the polymeric gel, while the indented regions may or may not include the polymeric gel. The polymeric gel acts as a sponge for a solutions or suspension of a molecular species. The raised regions of the patterned surface are immersed within one or more reservoirs for a solution or suspension of a molecular species. If desired, several reservoirs, each containing a unique molecular species, may be used to form an array of multiple molecular species. After the polymeric gel on the patterned surface has absorbed the molecular species from the reservoir(s), the patterned surface is pressed against a solid surface, thereby transferring the absorbed molecular species to that solid surface in a pattern corresponding to that of the patterned surface.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
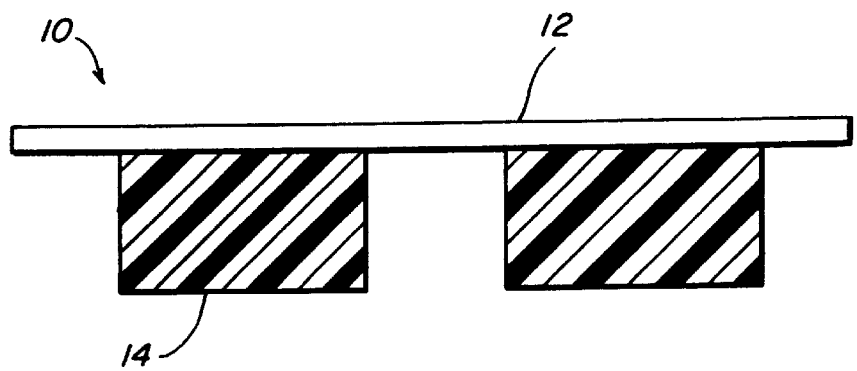
FIG. 1 shows a schematic cross-sectional view of an embodiment of the present invention.

The polymeric gel used in the present invention is matched to the type of molecule to be stamped and the solvent/vehicle in which molecular species is dissolved or suspended. The polymeric gel should have a sufficiently large quantity of the molecular species to permit a useful amount of the macromolecular to be transferred to other surfaces by stamping and to allow for repeated use of the stamp. The polymeric gel should not adhere or tear when placed against the surface to which the molecular species will be transferred. Also, the polymeric gel must allow the molecular species and its vehicle to flow out of the gel for transfer to the surface to be stamped. Additionally, the gel must be capable of polymerizing in a gel of arbitrary shape and irreversibly (e.g., covalently) binding to a substrate. Further the polymeric gel should have sufficient elasticity to conform to any roughness on the surface to be stamped so that a uniform molecular coverage will result over the patterned region. Moreover, the pore size of the polymeric gel should be larger than the size of the molecular species to be stamped, i.e., the molecular species to be stamped should be able to fit and flow within the pores of the substrate. Some typical polymeric gels useful in the method of the present invention have a mean pore size (diameter) of about 5 to about 200 nm, more often about 25 to about 100 nm. Most often, polymeric gels useful in the method of the present invention have an average pore size of about 35 to about 75 nm. One exemplary polymeric gel useful in the method of the present invention has an average pore size of about 50 nm.

Where the molecular species to be stamped is hydrophilic, the gel is typically a hydrogel. Particularly useful hydrogels are crosslinked polymers of acrylic acids esterified to a sugar and crosslinked polyacrylamides. Where the molecular species is hydrophobic, the polymeric gel may be a solvatogel including a lightly cross-linked polymer. In either case, the light crosslinking provides resiliency and structural definition to the gel, while the presence of large amounts of solvent (aqueous for a hydrogel or non-aqueous for a solvatogel) permits the polymeric gel to be sufficiently soft to conform to any roughness on the surface to be stamped. Typically, the polymeric gel is about 0.5% to about 10% crosslinked. More often, the polymeric gel is about 1% to about 5% crosslinked, and most often, the polymeric gel is about 2% to about 4% crosslinked.

The present invention may be used to stamp a substrate with any molecular species by selecting an appropriate solvent/liquid vehicle and polymer. Typically, the present invention is used to stamp macromolecules (about 1000 to about 150,000 Daltons) onto substrates. Typical macromolecules that may be stamped using the present invention include peptides, proteins, DNA, and palladium catalyst molecules.

Any surface may be used as a substrate in the method of the present invention. The substrate may be planar or non-planar. Typical substrates include glass, silica, silicon, and polystyrene. The molecule being stamped should be able to adhere to the substrate sufficiently to satisfy the purpose for which the stamped pattern is intended, such as the formation of a useful biosensor.

Any rigid surface to which the polymeric gel may be adhered, preferably irreversibly and preferably by covalent bonding, may be used as a backing support for the polymer gel. Typically, the backing support is planar, but planarity is not a requirement. For example, if desired, the backing support may take the form of a roller.

Figure 2:
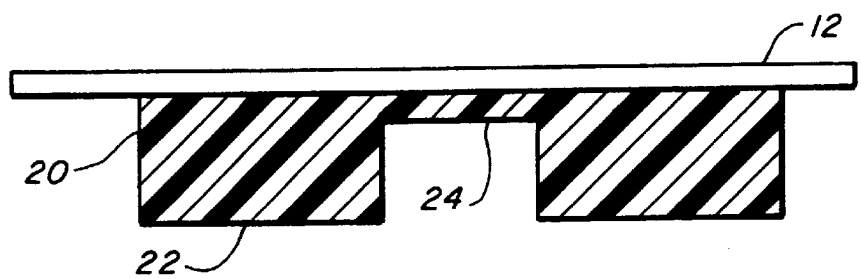
FIG. 2 shows a schematic cross-sectional view of another embodiment of the present invention.

FIG. 1 schematically illustrates one embodiment of a molecular stamp 10 according to the present invention. Here, polymer gels have been molded and lightly crosslinked to form pads 14. Pad or pads 14 is covalently bonded, by any known means, to backing 12, which has sufficient stiffness so that molecular stamp 10 may be used to stamp a substrate. Low portions 16, which are typically a regions devoid of polymeric gel, combine with pad or pads 14 to form an exposed patterned surface of raised portions and indented portions upon backing 12. Where a pattern including only one molecular species is to be formed, this pattern may be formed from a single piece of polymeric gel 20, adhered to backing 12, molded to include raised regions 22 and indented regions 24, as shown in FIG. 2. These raised and indented regions form an exposed patterned surface.

Once formed, molecular stamp 10 is "inked" by exposing it to a solution or colloidal suspension of macromolecule in a liquid vehicle appropriate for the stamp. The concentration of the macromolecule in the liquid vehicle is not particularly critical, as nanomolar (about 1 to about 100 nM) to millimolar (up to 1000 mM) concentrations and above may be used. Typically, the macromolecule is present in a millimolar concentration. The viscosity of the vehicle is not critical, provided that the macromolecule can diffuse through the vehicle at a sufficient rate to allow a practical stamping speed, and provided that the viscosity of the vehicles permits the polymeric gel to practically be exposed to and absorb the vehicle and macromolecule. This exposure may be accomplished by any means (e.g., soaking, dipping, or spraying) that allows the polymeric gel to absorb an a sufficient quantity of the solution or suspension to allow practical stamping of a desired number of substrates without additional inking. Preferably, the polymeric gel is saturated with the solution(s) or suspension(s) containing the macromolecule(s) of interest. If the molecular stamp for use in simultaneously stamping a pattern of multiple and distinct macromolecules onto a substrate, then care should be taken to avoid contamination of one raised section by a macromolecular intended for another raised section. For exposure by spraying, this contamination may be avoided by spraying each macromolecule into the raised sections through a mask, placed directly over the molecular stamp, having one or more windows aligned so that only pads intended to include that macromolecule are exposed to the spray. For exposure by soaking or dipping, an arrangement similar to that shown in FIG. 3 may be used.

Figure 3:
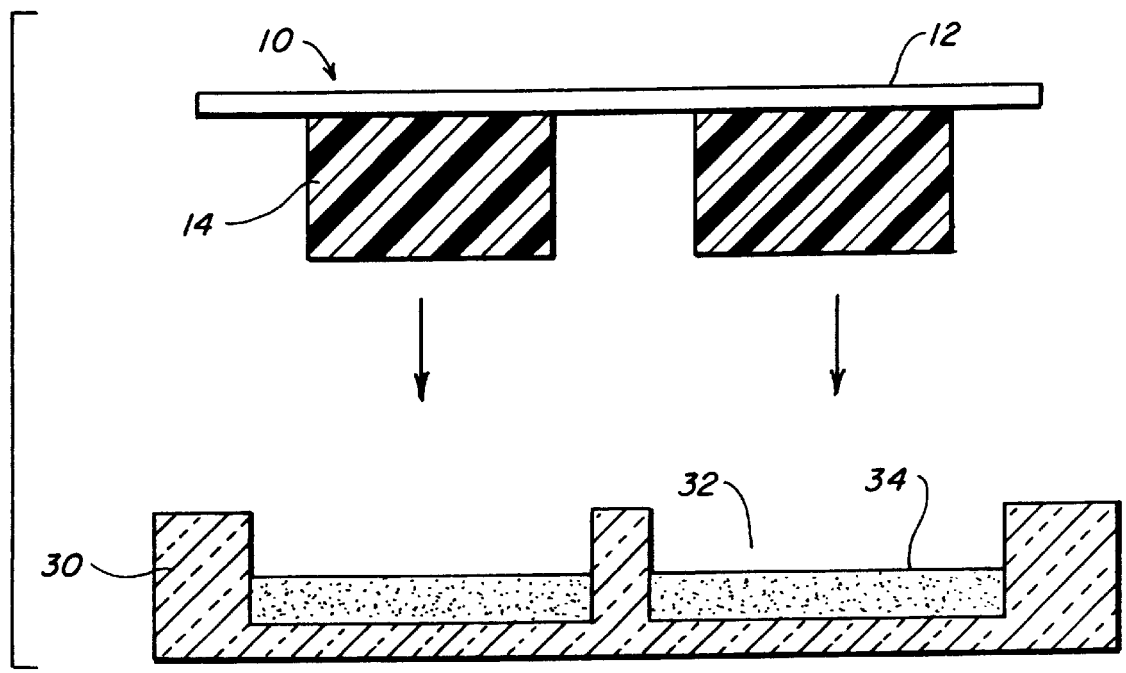
FIG. 3 illustrates, in schematic cross-sectional view, one method of loading macromolecules into a molecular stamp according to the present invention.

As shown in FIG. 3, tray 30 includes separate reservoirs 32 for each gel pad 14. Each reservoir 32 includes a suspension/solution 34 of the macromolecule of interest. If desired for producing multimacromolecular arrays, each reservoir 32 in tray 30 may include a different macromolecule of interest. As indicated by the arrows in FIG. 3, pads 14 are exposed to the suspension(s)/solution(s) 34 by inserting pads 14 into reservoirs 32. After pads 32 have been loaded with suspension(s)/solution(s) 34, microstamp 10, including pads 14, may be removed from reservoirs 32.

Figure 4:
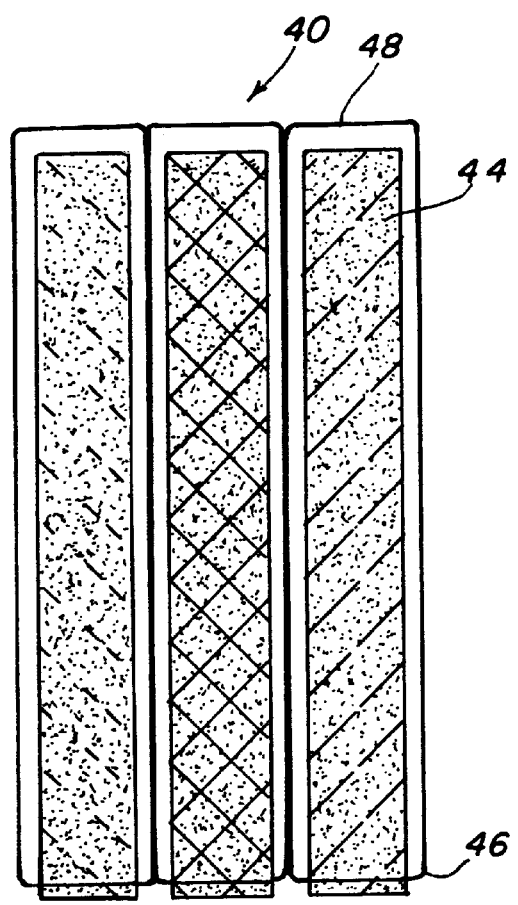
FIG. 4 shows a schematic cross-sectional view of an embodiment of the present invention in which the stamp is an array of microcapillary tubes filled with a polymeric gel.
Figure 6A:
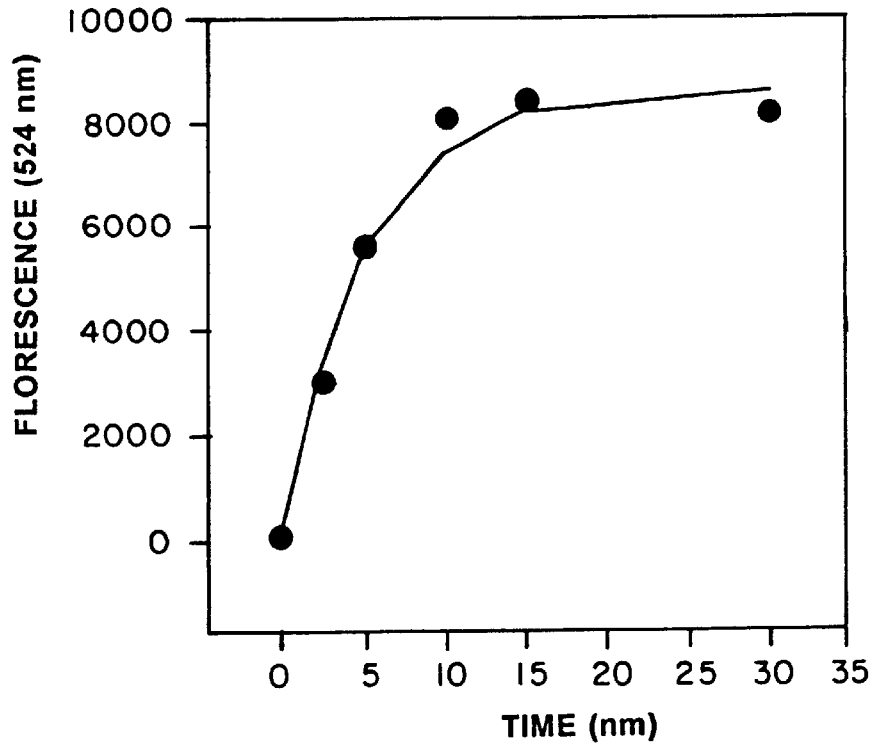
FIG. 6A through FIG. 6D are representative isotherms for fill of antimouse IgG-FITC into 2% (FIG. 6A) and 4% (FIG. 6B) crosslinked hydrogel films, and release of antimouse IgG-FITC from 2% (FIG. 6C) and 4% (FIG. 6D) crosslinked hydrogel films.
Figure 6B:
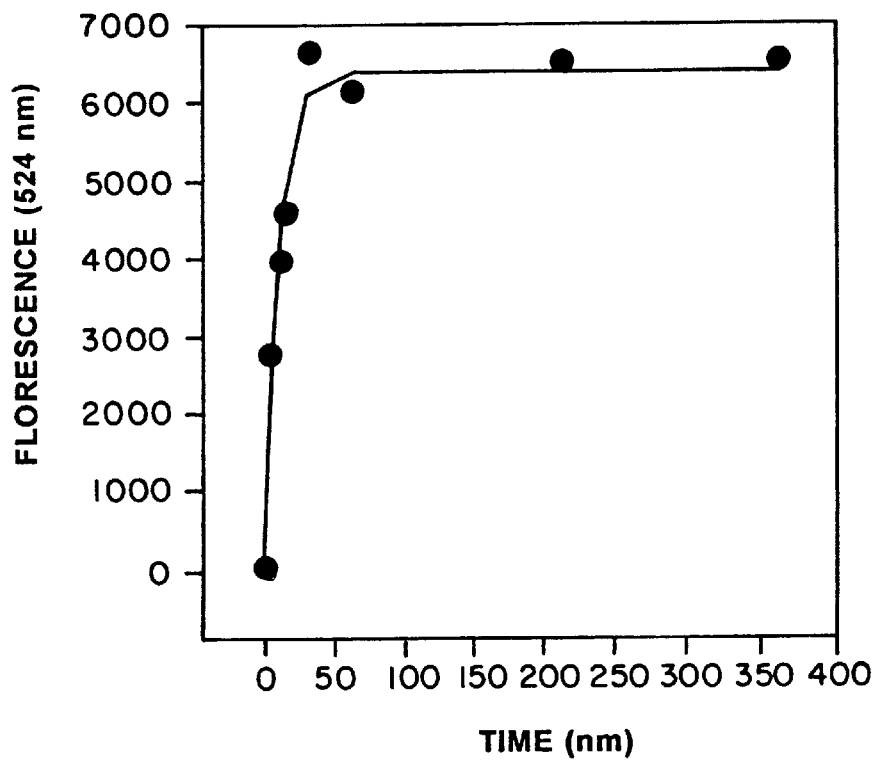
Figure 6C:
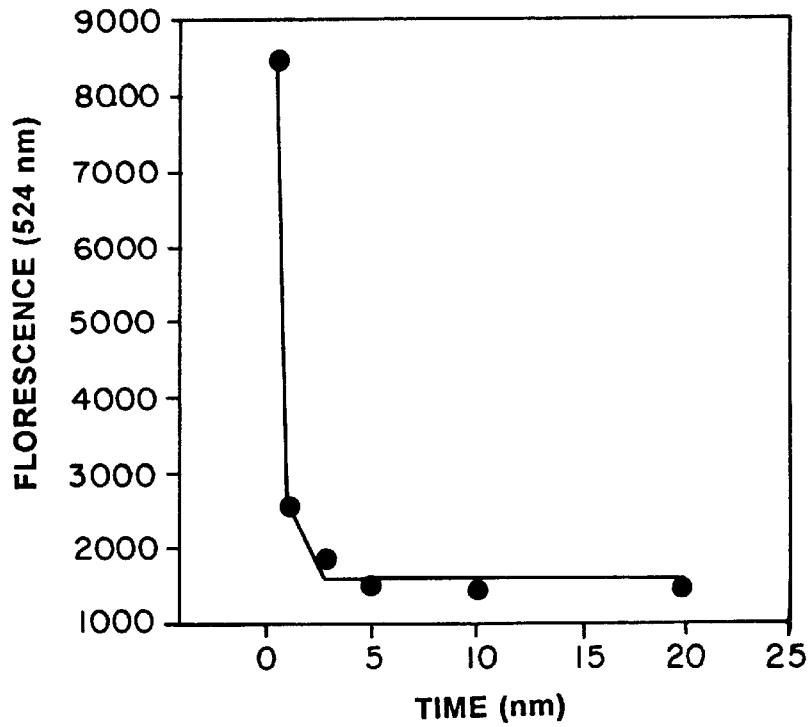
Figure 6D:
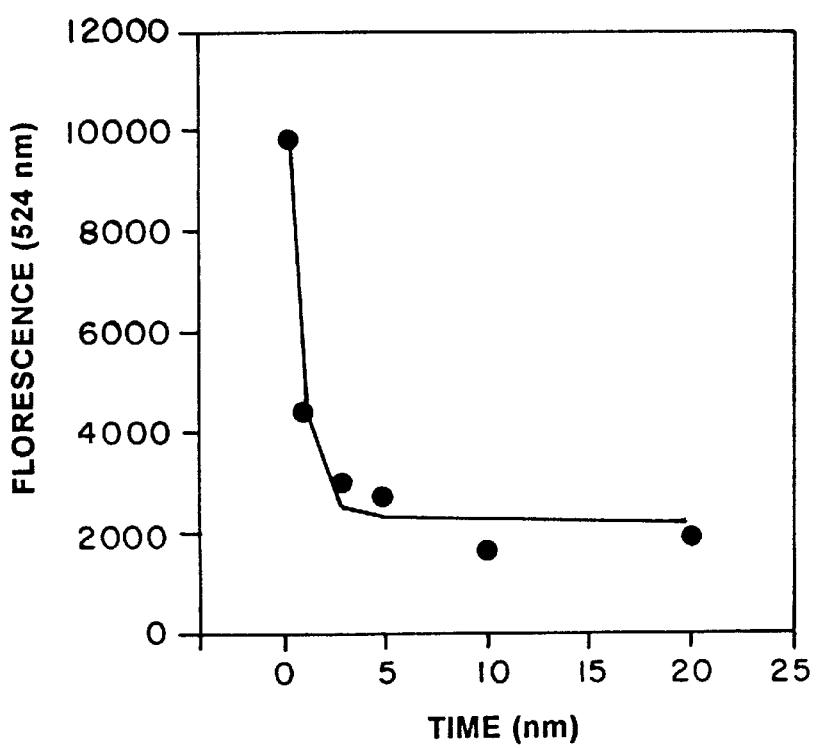

In another embodiment, shown in FIG. 4, stamp 40 is an array of microcapillaries 42 Typically, each microcapillary 42 has an inner diameter of about 10 μm to about 100 μm. Each microcapillary tube 42 is filled with polymeric gel 44 so that the gel extends beyond an open end 46 of the capillary. Opposite ends 48 of each capillary 42 are connected by capillary tubing (not shown) to individual reservoir (not shown). Each reservoir holds a solution/suspension of a molecular species of interest. Thus, each microcapillary 42 may be easily and continuously replenished from its own supply of a solution/suspension of a molecular species of interest. This arrangement facilitates repetitive stamping of a substrate surface.

Figure 5:
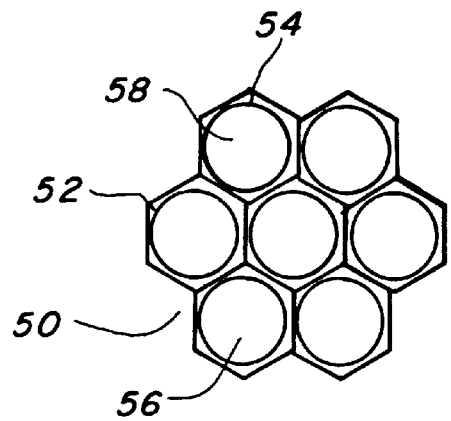
FIG. 5 is an end view of the embodiment shown in FIG. ?.

FIG. 5 shows an end view (taken from the stamping end) of another stamp according to the present invention. Stationary frame 50 includes cells 52. Microcapillaries 54, essentially identical to microcapillaries 42 from FIG. 4, are slidably disposed within cell 52 of frame 50. Each microcapillary tube 54 is filled with polymeric gel 56 so that gel 56 extends beyond an open end 58 of capillary 56. At their opposite ends, microcapillaries 54 are connected by capillary tubing (not shown) to individual reservoir (not shown). Each reservoir holds a solution/suspension of a molecular species of interest. Thus, each microcapillary 54 may be easily and continuously replenished from its own supply of a solution/suspension of a molecular species of interest. The axial movement of each microcapillary 54 within frame 50 is controlled by any suitable actuator, such as a piston (not shown). The axial motion of each microcapillary may be controlled independently or in groups. This arrangement allows one set of microcapillaries to stamp out a large number of different patterns.

For each embodiment, the molecular species is transferred to the substrate by contacting, e.g., by stamping, an exposed surface of the loaded polymeric gel with the substrate. For the transfer of thermally sensitive molecules, such as proteins, the substrate may be cooled (typically within a temperature range of above 0° C. to below 25° C., more often about 1° C. to about 20° C., and most often about 2° C. to about 10° C., with about 4° C. being an exemplary temperature) to reduce or prevent the possibility of denaturation or other forms of thermal degradation. Alternatively or additionally, the loaded suspension/solution of macromolecule may include a cryoprotectant such as trehalose, sucrose, glycerol, and poly(ethylene)glycol. Stamping may also be performed through a liquid drop or layer upon the substrate, if needed, to reduce the possibility of denaturation.

Having described the invention, the following examples are given to illustrate specific applications of the invention including the best mode now known to perform the invention. These specific examples are not intended to limit the scope of the invention described in this application.

EXAMPLES

Materials and Methods

N,N'-methylene-bis-acrylamide, *Pseudomonas fluorescens* lipase, bovine serum albumin (BSA) and monoclonal anti-mouse IgG (whole molecule) fluorescein (FITC) conjugate (1:128 dilution, ca. 1 mg/mL in 0.01 M phosphate buffered saline, pH 7.4, containing 1% BSA with 0.1% sodium azide, purified by immunospecific affinity chromatography) were obtained from Sigma Chemical Co. (St. Louis, Mo.), 2,2'-azobis[2-(2-imidazolin-2-yl)propane] dihydrochloride (AIPD) was obtained from Wako Pure Chemical Industries, Ltd. (Japan), and trimethoxysilylpropyl diethylenetriamine, methacryloxypropyltrimethoxy silane, pyridine and acetone were obtained from Aldrich Chemical Co. (Milwaukee, Wis.). The monomer 6-acryloyl-B-O-methylgalactoside and the hydrogel polymer were prepared according to literature procedures (28). Fused silica slides were obtained from NSG Precision Cells (Farmington, N.Y.). Deionized water was obtained using a Milli-Q filtration system.

Preparation of Hydrogel Films and Capillary Hydrogel

Fused silica slides (2.5 cm×2.5 cm) were cleaned by immersing the plates in 1:1 HCl:CH$_3$OH for 30 min, rinsing with deionized water, immersing in conc. H$_2$SO$_4$ for 30 min, rinsing with water, and finally heating them under water at 100° C. for 15 min. The slides were dried under a stream of N$_2$. The dried slides were then coated with methacryloxypropyltrimethoxy silane. The slides were silanized by adding 1 mL of the silane to 94 mL of a 1 mM solution of acetic acid in methanol in a N$_2$-filled dry box. This solution was removed from the dry box and 5 mL of water was added. The resulting mixture was poured into a Coplin jar containing the fused silica slides. After 15 min, the silane mixture was decanted and the slides were washed three times with methanol and then dried under a stream of N$_2$. The films were cured by drying overnight in the dry box at room temperature.

A 2.5 cm×2.5 cm piece of parafilm (100 μm thickness) with a 1 cm×1 cm center cut-out was placed on the silanized fused silica slides. 100 μL of the hydrogel reaction mixture (67.5 mg 6-acryloyl-B-O-methylgalactoside, 1.35 mg (2% crosslinking) or 2.70 mg (4% crosslinking) N,N'-methylene-bis-acrylamide and 3 μL of 5% aq. solution of AIPD in 382.5 μL water, degassed under vacuum for 8 min) was added to the 1 cm×1 cm×100 μm mold. The slide was then placed in a glass reactor and kept under N$_2$. The reactor was then lowered into an oil bath. The reactor was kept at 50° C. under N$_2$ for 30 min and then the slide was removed and allowed to cool to room temperature. The parafilm mold was then peeled away to reveal the hydrogel film. The hydrogel polymer network was a crosslinked poly(6-acryloyl-β-O-methylgalactoside), I, a highly hydrophilic polymer with ordered pendant-type sugar repeat units.

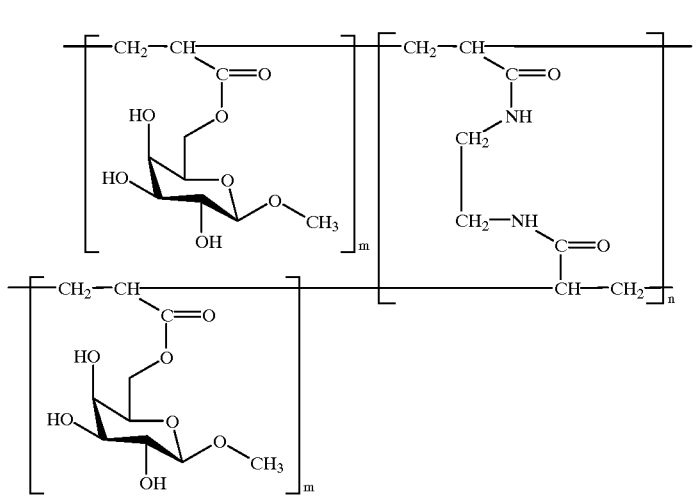

where m and n are integers and the average ratios of m to n varies from 1000 to 20, corresponding to crosslinker mole fraction variation from 0.2 to 5.0 mole %. Elasticity measurements indicate that I has average network mesh-sizes of above 50 nm when swollen in aqueous solution and solute diffusion behavior in I and closely-related gels suggest that the polymer experiences minimal protein adsorption. These traits indicated that I was well suited as a vehicle for delivery of small amounts of protein. The capillary hydrogel was prepared in flame-drawn glass capillary tubes with narrow-end IDs of 30 to 100 μm as described above for the silanized fused silica slides.

Transport Experiments

All transport experiments were performed at 23° C. The hydrogel films or capillary hydrogel were hydrated in water overnight and then immersed in the monoclonal anti-mouse IgG-FITC solution (4 mL, 8-fold dilution of stock solution with water) to begin the filling process. Immersion time before beginning release measurements for both the films and the capillary hydrogels was 15 min. In the case of the films, the slides were placed in a 3.5 cm×0.5 cm polystyrene dish and the dish was covered to minimize any effects from evaporation. None of the outer reservoir solutions were stirred because the solutions used to fill the capillary hydrogel and through which the protein was to be transferred to the silica surface would not be stirred. The solution was agitated during loading and removal of the slide into and from the dish. After a predetermined time, the slides were removed from the antibody solution, rinsed with water and the hydrogel fluorescence was measured at 524 nm using a SLM 8000 fluorimeter. The fluorescence beam was set orthogonal to the plane of the hydrogel films and capillary hydrogel. The wavelength of 524 nm was chosen for monitoring the fluorescence based on the emission spectrum of anti-mouse IgG-FITC on a fused silica slide. The hydrogels were then reimmersed into the antibody solution until the time for the next measurement. Care was taken to minimize the time that the hydrogels were out of the antibody solution in order to prevent significant drying. Measurements were made until the fluorescent readings reached a plateau. Then, the hydrogel films were immersed in 4 mL water and the release of the antibody was monitored in a similar manner. After each experiment with the hydrogel films, each film was carefully removed from the silanized fused silica slide and the residual fluorescence on the slide was measured. A minimum of three isotherms for both uptake and release were acquired in this manner. Release data for capillary hydrogel were gathered separately from the uptake data. The capillary was immersed in the antibody solution described above in a capped glass vial for 15 min and then immersed in 4 mL water. Data were then collected as described for the films. Great care was taken to position the capillary in the fluorimeter so that the beam passed through the same portion of the capillary for each measurement. Six isotherms for both uptake and release of antibody were acquired.

Calculations

Fluorescence uptake and release data for the hydrogel film and the capillary encapsulated hydrogel was fit to an exponential of the form $$f = f_0(1-e^{-t/\tau}) \text{ (uptake) and } f = f_0 e^{-t/\tau} \text{(release)}, \quad (1)$$

where $f$ was the measured fluorescence intensity, $f_0$ was the starting fluorescence for the release data or the asymptotic fluorescence for the uptake data, and $\tau$ is the characteristic decay time.

Diffusion constants (D) for hydrogel release were calculated using the one dimensional diffusion equation with the solution, $$\frac{C(t)}{C_0} = \frac{8}{\pi^2} \sum_{n=0}^{\infty} \frac{1}{(2n+1)^2} e^{-\frac{(2n+1)^2 \pi^2}{4L^2} Dt}, \quad (2)$$

where C(t) is the concentration of protein as a function of time, $C_0$ is the concentration in the gel at time t=0, and L is the thickness of the gel. For the hydrogel films, L=100 mm and for the capillary hydrogel, L=1.2 cm. For sufficiently large t the higher order terms can be neglected. So at time $t_{1/2}$, when $C(t)/C_0 = \frac{1}{2}$, we have:

$$D = \frac{4}{\pi^2} \ln\left(\frac{16}{\pi^2}\right) \frac{L^2}{t_{1/2}} = (0.1958) \frac{L^2}{t_{1/2}}. \quad (3)$$

Hydrogel uptake data were calculated using a trivial modification of equation (2) which also yields equation (3) for the determination of D. Diffusion constants for the capillary release and fill data were also calculated using equations (2) and (3), where in this case L is the length of the hydrogel region in the capillary. The one-dimensional diffusion equation was used because diffusion of material was limited to flow along the length of the capillary to the end. To calculate D, $t_{1/2}$ was taken from the experimental fits in eq. 1 ($t_{1/2}$=tln2) and was substituted into eq. 3.

Transfer of Antibody to Silica Surface

Fused silica plates were chemically modified with an aminosilane (trimethoxy-silylpropyl diethylenetriamine) as described above for the preparation of methacryloxypropyltrimethoxy silane coated slides to enhance reception of the antibody. The capillary hydrogel was immersed in monoclonal mouse anti-FITC (8-fold dilution of stock solution with water, ca. 1 mg/mL) for 30 min. The hydrogel swelled slightly from solution uptake, causing the tip to extrude from the end of the capillary. The extruded hydrogel tip was then brought into short contact (ca. 1 s) with the DETA coated silica plate through a small water droplet. The capillary was withdrawn, positioned over a second droplet, and the process repeated. The water droplets were used to ensure that the deposited antibody did not dry on the surface and denature. Following the deposition of the antibody spots, the plate was immersed in a bovine serum albumin (BSA) solution (1:1000 wt:wt) to block non-specific binding on the remaining areas of the surface. The plate was washed and immersed in a solution containing FITC-conjugated BSA (antigen). The plate was washed a final time and observed using fluorescence microscopy.

Results and Discussion

The formation of the hydrogel films was straightforward. Typically, the water content of the hydrogels immediately following their preparation was ca. 85%. Upon hydrating the 2% and 4% crosslinked gels overnight, water content is known to increase to 97.3% and 90%, respectively. Representative uptake and release profiles obtained for the transport of monoclonal anti-mouse IgG-FITC into and out of the thin 2% and 4% crosslinked hydrogel films are presented in FIG. 6A through FIG. 6D. The uptake and release of antibody from the hydrogels was modeled on diffusion processes to give the average diffusion coefficients listed in Table 1. The values of D are similar to those obtained for the diffusion of the protein through water ($6.29 \times 10^{-7}$ cm$^2$/s) as well as the release of similarly sized proteins through hydrogels prepared from other materials indicating that protein transport through the 2% and 4% crosslinked hydrogel films is a largely diffusion controlled process. However, the release rates are consistently faster than the fill rates. One possible explanation for this behavior involves the effect of the differences in solute concentration between the reservoir and hydrated gel. The protocol for the transport experiments was designed to mimic the conditions under which a capillary hydrogel would be loaded with protein and used in transferring the protein to a silica surface. Because the protein would be loaded into capillary hydrogels hydrated in water, all of the hydrogels used in the transport experiments were hydrated in water and not buffer. In addition, the protein was to be transferred to the silica surface through a water droplet and therefore the outer reservoir solution for all release experiments was water. The swelling of the hydrogel would be affected by any resulting differences in solute concentration between the outer reservoir and the hydrogel film. As solute concentration in the medium is increased, gel swelling decreases slightly. In the protein filling process the hydrogel film initially contains deionized water when it is immersed in large reservoir of protein/buffer. The resulting solute concentration differences set-up an osmotic potential which draws water from the hydrogel to the buffer phase causing gel contraction and a pore size decrease which impedes entry of protein. Conversely, in the protein release process the hydrogel film initially contains protein/buffer when it is immersed in a large reservoir of deionized water. Water is osmotically drawn into the gel, swelling occurs, pore sizes increase and protein release is facilitated.

The swelling of similar neutral sugar-based hydrogels has been demonstrated to be essentially independent of pH from 1.5 to 8. Therefore, effects resulting from differences in the pH of the reservoir (pH 7.4 during filling process and pH 5.5 during release process) and the film (pH 5.5 during the filling process and pH 7.4 during the release process) are probably negligible. It should also be noted that the fluorescent label of the antibody is hydrophobic which may cause the anti-mouse IgG-FITC conjugate to diffuse more rapidly through the hydrophilic environment of the hydrogel than would be the case for the non-labeled antibody.

The residual fluorescence observed for the protein release isotherms reflect the amount of non-specific binding of the protein to the silica plates as determined by measuring the fluorescence of the plates minus the hydrogel film at the completion of each release experiment. In each case the plate fluorescence equaled the residual fluorescence. Therefore, under the conditions of these experiments, no protein remains entrapped in the hydrogel after release is complete. This is a very important point in that it demonstrates that protein is not adhering to the gel or becoming entangled in any sidechains within the gel. Also, the results for each 2% and 4% crosslinked hydrogel film indicate that the pores produced during hydrogel crosslinking are consistently large and probably homogeneous from preparation to preparation. Thus, the results demonstrate that the pore structure and chemical nature of the hydrogel do not hinder the rapid, free flow of the protein through the 2% and 4% crosslinked gels.

Based solely on the filling and release profiles and the calculated diffusion coefficients, either the 2% or 4% crosslinked hydrogel would be a suitable choice for forming the capillary hydrogel that will be used as the protein transfer "sponge". The 2% hydrogel, however, was found to be the most appropriate for several reasons. The 2% crosslinked hydrogel was handled and manipulated repeatedly without any resulting damage to the gel. Increasing the crosslinking from 2% to 4% resulted in increased fragility of the hydrogel. In addition, in some cases the hydrogel may have to be extruded through the capillary in order to have a small piece of the gel protrude from one end of the capillary to form a contact point for protein transfer to a surface. Because the lower crosslinked hydrogel is more elastomeric and more stable to handling, the 2% hydrogel would be a better choice to form the capillary hydrogel.

Figure 7A:
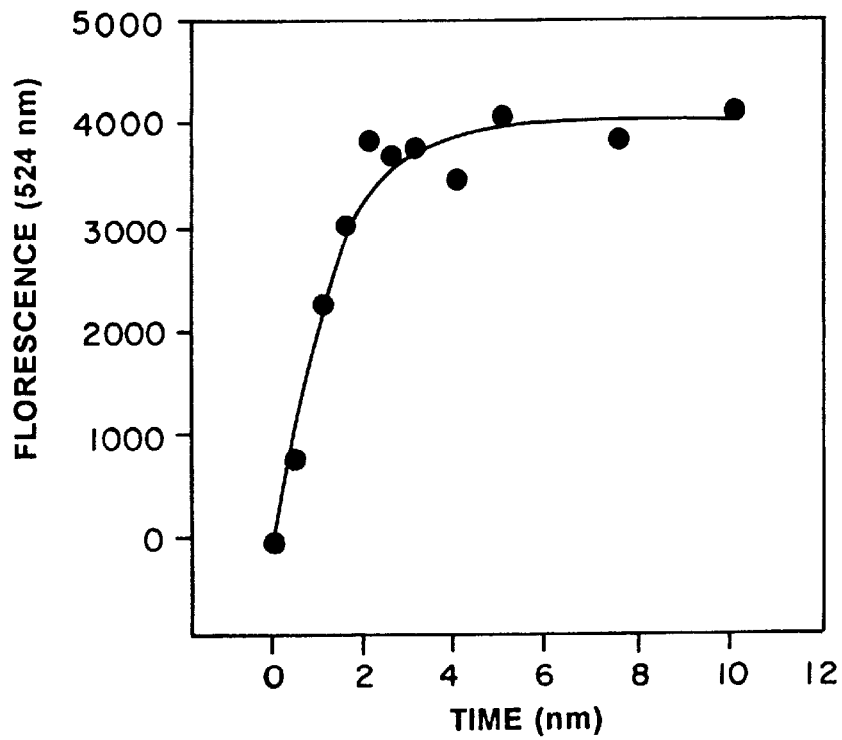
FIG. 7A and FIG. 7B are representative isotherms for fill (FIG. 7A) and release (FIG. 7) of antimouse IgG-FITC into and from capillary hydrogel.
Figure 7B:
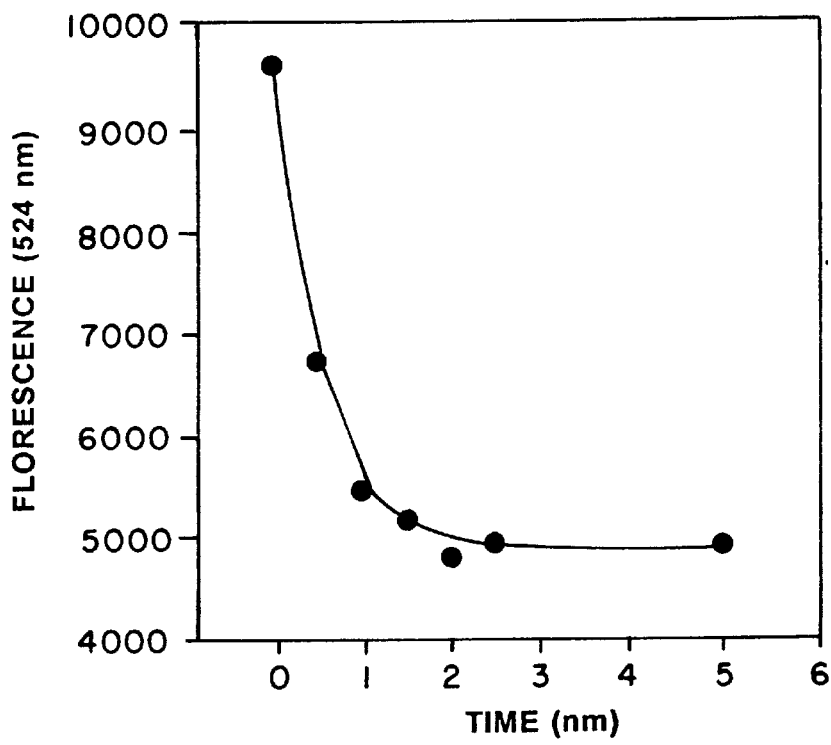

Representative filling and release profiles obtained for monoclonal anti-mouse IgG-FITC transport into and out of the capillary hydrogel are shown in FIG. 7A and FIG. 7B. The capillary hydrogel was formed directly inside the capillary. Differences in the maximum fluorescence observed between the uptake and release profiles result from differences in the positioning of the capillary in the fluorimeter. Care was taken to maintain capillary positioning throughout each individual experiment. The results demonstrate the stability of the capillary hydrogel to repeated use. The results also demonstrate that, as with the hydrogel films, a rapid free flow of antibody through the hydrogel was achieved. In fact, diffusion coefficients calculated for the transport of the antibody through the hydrogel ($D=7.4 \times 10^{-3} \pm 2.3 \times 10^{-3}$ cm$^2$/s for filling and $1.3 \times 10^{-2} \pm 2.0 \times 10^{-3}$ cm$^2$/s for release) were several orders of magnitude greater than would be anticipated for a process involving a simple diffusion mechanism. One possible explanation for the accelerated transport behavior is the influence of tip hydration. In contrast to the 2% crosslinked hydrogel film (1 cm×1 cm×100 $\mu$m), only a small piece of the gel protruding from one end of the capillary (ca. 30 $\mu$m diameter×1.2 cm length) was directly exposed to aqueous filling or release reservoirs. The extent of the protrusion from the capillary depends on the state of hydration of the gel. As with the films, data was obtained using a non-continuous assay which involved removing the capillary from the reservoir for fluorescence measurements and then reimmersing the capillary back into the reservoir until it was time for the next measurement. Due to the differential in size between the capillary hydrogel and the hydrogel films, it is reasonable to assume that the relative degree of drying in the extruded portion of the capillary hydrogel would be much greater than that for the hydrogel films. Consequently, the capillary hydrogel will be subjected to the effects of dehydration to a much greater degree than the hydrogel films. This dehydration and subsequent rehydration with water and/or protein molecules cause a rapid swelling of the hydrogel which draws in water and protein molecules at super-diffusional rates. Thus, antibody uptake/release will be significantly greater than for simple diffusion of the protein into a capillary hydrogel with a constant level of hydration. In fact, a fully dehydrated capillary hydrogel draws in protein and water rapidly and fills the gel in a matter of seconds. The rate of filling for the dehydrated hydrogel was much too fast to obtain sufficient data points to measure a diffusion constant given the limitations of our experimental protocol.

In order to test whether or not the capillary hydrogel would transfer the antibody to a surface, an antibody loaded capillary hydrogel (30 mm diameter tip) was brought into contact with a "sticky" aminosilane (DETA: trimethoxysilylpropyl diethylenetriamine) coated fused silica plate within a water droplet on the surface of the plate. After removal of the capillary, the remaining plate surface area was blocked with BSA and then the antigen, FITC-conjugated BSA, was added. A representative circular micropattern was obtained via fluorescence microscopy. The pattern arose from FITC-BSA bound to the transferred monoclonal anti-mouse IgG-FITC, and clearly indicated that the antibody remained active after the transfer. The average and peak fluorescence intensities of the circular region were 14.1 and 19.6 times greater than background, indicating good transfer of active antibody to the surface at reasonably high spatial resolution (~5 $\mu$m). No transfer of the hydrogel to the surface was observed. The same hydrogel tip could be used at least 3 times without reloading for significant transfer of protein to the silica surface.

Additional Studies of IgG Transfer

The stamper was constructed by forming the hydrogel within the narrow ends of automechanically-pulled capillary tubes. The tubes were immersed in water wherein the gel swelled to equilibrium, permitting diffusional removal of unreacted monomer with concomitant gel extrusion. The assembly was freeze-dried and any extruded polymer was removed, leaving the remainder of the dry polymer as a "nib" positioned in the endmost portion of the capillary tip. Typically, antibody solution of 0.10 wt % IgG in PBS was loaded into the dry gel I via a 40 micron OD feed line, causing gel rehydration/reextrusion.

An aminosilylated receiving surface (typically coated fused silica or silicon wafer was placed on the stage and allowed to cool to an equilibrium temperature of 4–6° C. The stamping was performed by slowly lowering the gel/ capillary towards the receiving surface until the threshold of conformal contact occurred. It was retained for ca. 1 sec, allowing protein to deposit in a circular region. The stamper was raised and the surface was shifted by micropositioning in preparation for the next "stamp", which was delivered in a manner identical to the first. The procedure was repeated until all desired pattern elements were formed. Typical arrangements were "L"-shaped and composed of four solid circular elements. In some cases, a total of three IgG isotypes were "stamped" into adjacent surface regions.

Upon completion of micropatterning the surface was washed and blocked with BSA for passivation of nonpatterned regions. It was then exposed to PBS containing fluorescently-labeled antigen complementary to the stamped IgG. Patterns were visualized and recorded via confocal fluorescence microscopy. When multiple IgGs were deposited, antigen exposure and visualization were sequential.

A primary asset of the stamper is its ability to enable rapid, simple fabrication of protein microarrays. Sequential patterning and visualization (20×magnification) of multiple IgGs was thus undertaken. Rabbit anti-goat (A), Rabbit anti-mouse (B), and goat anti-human (C) IgG arrays were constructed and sequentially exposed to the corresponding FITC-labeled antigens. In each case, the 3D-shape of an individual stamper is manifested as a characteristic 2D-shape apparent in each pattern element. The average fluorescent signal-to-background ratios of the A, B, and C micropatterns were 37.0±8.3, 29.1±4.6, and 34.3±6.4, respectively. For comparison, the IgGs were deposited on identical surfaces from droplets of IgG solution of the same composition as that of the stampers, and exposed to labeled antigen. The signal-to-background ratios arising from this process are 53.5±22.2, 38.9±10.4, and 42.8±17.0, respectively. These results suggest that the stamper was able deliver an average amount of active IgG corresponding to 74.3% of that attainable from sessile droplets, with an average variation of ±11.5%. The stamped RAM and GAH IgGs (left-hand patterns) absorbed a small amount of labeled goat IgG, presumably because of non-specific interactions. The average NSA-to-background ratios for the stamped RAM and GAH patterns are 7.03±1.22 and 9.08±1.06 respectively, and the resulting signal-to-NSA ratio for the stamped RAG pattern (right-hand side) is 4.89±1.78.

Several other patterns were stamped using additional IgGs showing that the images can be placed in close proximity (ca. 10 micron edge distance), and local size variations can be attained. The results also demonstrated that patterns can be formed by stamping through a resting droplet of DI water.

The surface density and thickness of a stamped rabbit anti-goat IgG film were directly measured using radiolabeled IgG and atomic force microscopy (AFM). The radioactivity level of $I^{125}$-labeled IgG delivered from a sessile droplet represented a density of 548±46.8 ng/cm$^2$ whereas the density of stamped labeled IgG was found to be 286±10.7 ng/cm$^2$, corresponding to a relative surface coverage of 52.2%±5.90% (45). The stamper therefore accomplishes protein delivery as a ca. half-monolayer. An AFM image of a stamped region indicates an average height of 0.76 nm (±0.13) above the neighboring bare surface, and a stamp roughness of about 150% greater than this surface. These characteristics suggest sub-monolayer deposition in agreement with the radiological data.

Proteins in a highly-packed surface layer can experience lowered avidity because of intralayer steric interactions. Also, many binding sites may be blocked due to neighboring bound antigen or the tight packing may force the protein into a narrow distribution of conformations, reducing specific activity. The submonolayer deposition by the stamper does not impose such restrictions and may afford a higher binding capacity per IgG, i.e., compare approximately 75% surface activity versus only 52% surface coverage. It should also be noted that it is possible to modify the stamping conditions, if necessary, to increase the surface packing density. For example, one could increase the contact time or the concentration of protein within the stamper gel.

For future applications, several stampers could be bundled into a single assembly to provide a rapid, parallel fabrication route for 2-D protein arrays such as those needed in next-generation immunosensors and in relatively unexplored technologies such as bioelectronics. Also, single stampers could also be of assistance in cell patterning in vitro, either by allowing selective attachment of cells (e.g, via the cell membrane or cell wall) to antibody-patterned surfaces, or by selective delivery of a bioactive agent to a selected pattern of cells. For example, selected cells in a 2-D culture could receive a "stamp" providing a dosage of hormones or cytokines, leading to selective differentiation. In that application, and others, the stamp serves a device for delivering biologically active compounds to cells by contact therewith. Hormones, cytokines, nucleic acids, etc, could all be delivered in this manner to control any number of cellular events. Also, the ability to deliver a half-monolayer of protein per application suggests that sequential stamping of different proteins onto a single region will enable construction of 3-D protein ensembles. This feature, in turn, allows the production of a distinct spatial arrangement capable of carrying out a multiple step enzymatic process on a substrate in solution.

Obviously, many modifications and variations of the present invention are possible in light of the above teachings. It is therefore to be understood that, within the scope of the appended claims, the invention may be practiced otherwise than as specifically described.

What is claimed is:

1. A molecular stamp comprising:
   a solid substrate support;
   a polymeric gel covalently bound to said solid support so as to form an exposed patterned surface, said patterned surface including a raised region comprising said polymeric gel and at least one indentation within said raised region;
   said polymeric gel having absorbed therein a liquid vehicle, said liquid vehicle having a first molecular species dissolved or colloidally suspended therein.

2. The molecular stamp of claim 1, wherein said polymeric gel is a hydrogel.

3. The molecular stamp of claim 2, wherein said indentation is defined by an absence of said polymeric hydrogel.

4. The molecular stamp of claim 3, wherein said raised region comprises at least two distinct raised portions comprising said polymeric hydrogel, said at least two raised portions being isolated from each other by said indentation.

5. The molecular stamp of claim 2, wherein said molecular species is a biomolecule.

6. The molecular stamp of claim 5, wherein said molecular species is a protein.

7. The molecular stamp of claim 2, wherein said polymeric hydrogel is a sugar-based polyacrylate hydrogel.

8. The molecular stamp of claim 7, wherein said polymeric hydrogel is formed by crosslinking 6-acryloyl-β-O-methylgalactoside.

9. A molecular stamp comprising an array of capillaries, each of said capillaries having an open end, a plurality of said capillaries each including therein a gel extending from within said capillaries to beyond said open end of said capillaries, said gel in at least one of said capillaries having absorbed therein a liquid vehicle having a first molecular species dissolved or colloidally dispersed therein.

10. The molecular stamp of claim 9, wherein said capillaries are in fluid connection with a reservoir including said liquid vehicle and said first molecular species dissolved or colloidally dispersed therein.

11. The molecular stamp of claim 9, wherein said molecular species is a biomolecule.

12. The molecular stamp of claim 11, wherein said molecular species is a protein.

13. The molecular stamp of claim 9, wherein said gel is a hydrogel.

14. The molecular stamp of claim 13, wherein said polymeric hydrogel is a sugar-based polyacrylate hydrogel.

15. The molecular stamp of claim 14, wherein said polymeric hydrogel is formed by crosslinking 6-acryloyl-β-O-methylgalactoside.

16. The molecular stamp of claim 9, wherein said gel in another one of said capillaries has absorbed therein a second molecular species, said second molecular species being distinct from said first molecular species, and wherein each of said capillaries has only one molecular species dissolved or suspended in said liquid vehicle absorbed therein.

17. A method of transferring a molecular species to a substrate, said method comprising the steps of:

loading a molecular species dissolved or colloidally suspended in a liquid vehicle into a polymeric gel, said polymeric gel being covalently bound on one surface thereof to a solid support so as to form an exposed patterned surface on another surface of said gel, said patterned surface including a raised region comprising said polymeric gel and at least one indentation within said raised region;

contacting said exposed portion of said polymeric gel to a substrate, thereby transferring said loaded molecular species from said polymeric gel onto said substrate.

18. The method of claim 17, wherein, during said contacting step, said substrate is at a temperature of above 0° C. and below about 10° C.

19. The method of claim 17, wherein said polymeric gel is a hydrogel and said indentation is defined by an absence of said polymeric hydrogel.

20. The method of claim 19, wherein said raised region comprises at least two distinct raised portions comprising said polymeric hydrogel, said at least two raised portions being isolated from each other by said indentation, and wherein said molecular species loaded in one of said at least two raised regions is a different molecular species than the molecular species loaded in the other one of said at least two raised regions.

21. The method of claim 17, wherein said substrate is a live cell.

\* \* \* \* \*